United States Patent [19]

Trees

[11] Patent Number: Plant 6,657

[45] Date of Patent: Mar. 7, 1989

[54] VARIETY OF GERANIUM NAMED SABRINA (OGLEVEE NO. 126)

[75] Inventor: Scott C. Trees, Elburn, Ill.

[73] Assignee: PanAmerican Seed Company, West Chicago, Ill.

[21] Appl. No.: 95,452

[22] Filed: Sep. 10, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Ziesenheim & Webb

[57] ABSTRACT

The new cultivar is characterized by its unique coral red color and its densely packed umbel giving the overall effect of semi-doubleness. It is further characterized by its free basal branching, compact growth, and free continuous and early flowering.

1 Drawing Sheet

BACKGROUND OF THE INVENTION

The present invention comprises a new and distinct cultivar of *Pelargonium hortorum bailey* known by the varietal name Sabrina (Oglevee No. 126). The new variety was discovered in a selective breeding program in April of 1982 in West Chicago, Ill. The new variety is a first generation selfed progeny of the variety Morgengrus. The new variety was first asexually reproduced by cuttings at Pan American Seed Company in West Chicago, Ill. on or about November of 1983. The new variety has been repeatedly asexually reproduced by cuttings at Oglevee Floral Company in Connellsville, Pa. over a several year period. It has also been trial and field tested at Connellsville and has been found to retain its distinctive characteristics through successive propagations.

The new variety has large round umbels of single florets with similar pedicel length and zoned foliage when compared to Morgengrus. The new variety differs from Morgengrus in that the petal color has a more unique coral red color as compared to the salmon color of Morgengrus. In addition the more densely packed umbel gives the overall effect of semi-doubleness.

The new cultivar when grown in a glass greenhouse in Connellsville, Pa. using natural light and 60° F. (night), 68° F. (day) and 71° F. (vent) has a response time of six weeks from a rooted cutting to flowering in a 10 cm pot. This response time was determined on plants grown in a soilless media employing constant fertilizer of 275–300 parts per million nitrogen and potassium and in full light.

DESCRIPTION OF THE DRAWING

FIG. 1 of the accompanying photographic drawing illustrates a new cultivar, the color being as nearly true as possible with color illustrations of this type.

DESCRIPTION OF THE NEW PLANT

The following detailed description sets forth the characteristics of the new cultivar. The data which define these characteristics were collected by asexual reproductions carried out by the Oglevee Floral Company in Connellsville, Pa. The plant history was taken on six week plants blossomed under natural light in a greenhouse and color readings were taken indoors under 200–220 foot candles of cool, white fluorescent light. Color references are primarily to the R.H.S. Colour Chart of The Royal Horticultural Society of London.

THE PLANT

Classification:

*Botanical.*—*Pelargonium bailey.*

*Commercial.*—Zonal geranium.

Form: Semi-dwarf; free basal branching; compact growth; flowers close to foliage; free continuous and early flowering.

Height: 21.0–32.0 cm from media surface.

Growth: Free basal branching; short internodes; compact.

Strength: Stands upright without artificial support.

Foliage: Stalked leaf attachment; leaf zoning.

Leaves:

*Size.*—6.0–9.0 cm across.

*Shape.*—Reniform; cordate base.

*Margin.*—Crenate.

*Texture.*—Pubescent; dull (Non-reflective).

*Color.*—Top: Margin — Green group 143B; Center — Green group 143B. Zone: Green group 137B; Bottom: Yellow-Green group 144B.

*Ribs and veins.*—Palmate; Yellow-Green group 144D.

Petioles: 4.0–7.0 cm in length; Yellow-Green group 144A.

Stem:

*Color.*—Yellow-Green group 144B.

*Internodes.*—1.0–3.0 cm in length.

THE BUDS

Shape: Hemispherical cluster.

Size: 2.0–3.0 cm across.

INFLORESCENCE

Blooming habit: Continuous; upright; semi-double appearing; some shattering; hemispherical.

Size: 7.0–11.0 cm across.

Borne: Umbel; florets on pedicel; pedicels on peduncle.

Florets:

*Form.*—Flat to slightly cupped; ovate.

*Color.*—Top: Margin — Red group 41C; Center — Red group 41B. Bottom: Red group 41C. Petals: 5 in number; separate — not united; margin entire, obovate; palmate veination; flat to slightly cupped; 1.0–2.5 cm across.

*Size.*—3.0–5.0 cm across.

*Texture and appearance.*—Smooth and reflective.

Petaloids: Quantity: none observed.

Pedicel:

*Length.*—1.5 to 3.0 cm.

*Color.*—Greyed-Red group 181C.

Peduncle: Yellow-Green group 144A; 12.0–16.0 cm in length.

REPRODUCTIVE ORGANS

Stamens:

*Anthers.*—Initially reddish-purple.

*Filaments.*—Very pale green at base to reddish-purple toward tip; irregular in shape; 3.0–5.0 mm in length; flat.

*Pollen.*—Golden brown initially.

Pistils:

*Number.*—1 with 4–5 parted stigma.

*Length.*—1.0 cm.

*Stigma.*—4–5 parted; reddish-purple.

*Style.*—1; pale green; initially reddish-purple at maturity.

Ovaries: 5.0 mm in length; yellow-green; very pubescent (0.1 to 0.5 mm long); superior.

Fruit: none observed.

The new cultivar is characterized by its unique coral red color and its densely packed umbel giving the overall effect of semi-doubleness. It is further characterized by its free basal branching, compact growth, and free continuous and early flowering.

I claim:

1. A new and distinct variety of geranium plant substantially as shown and described and parts thereof.

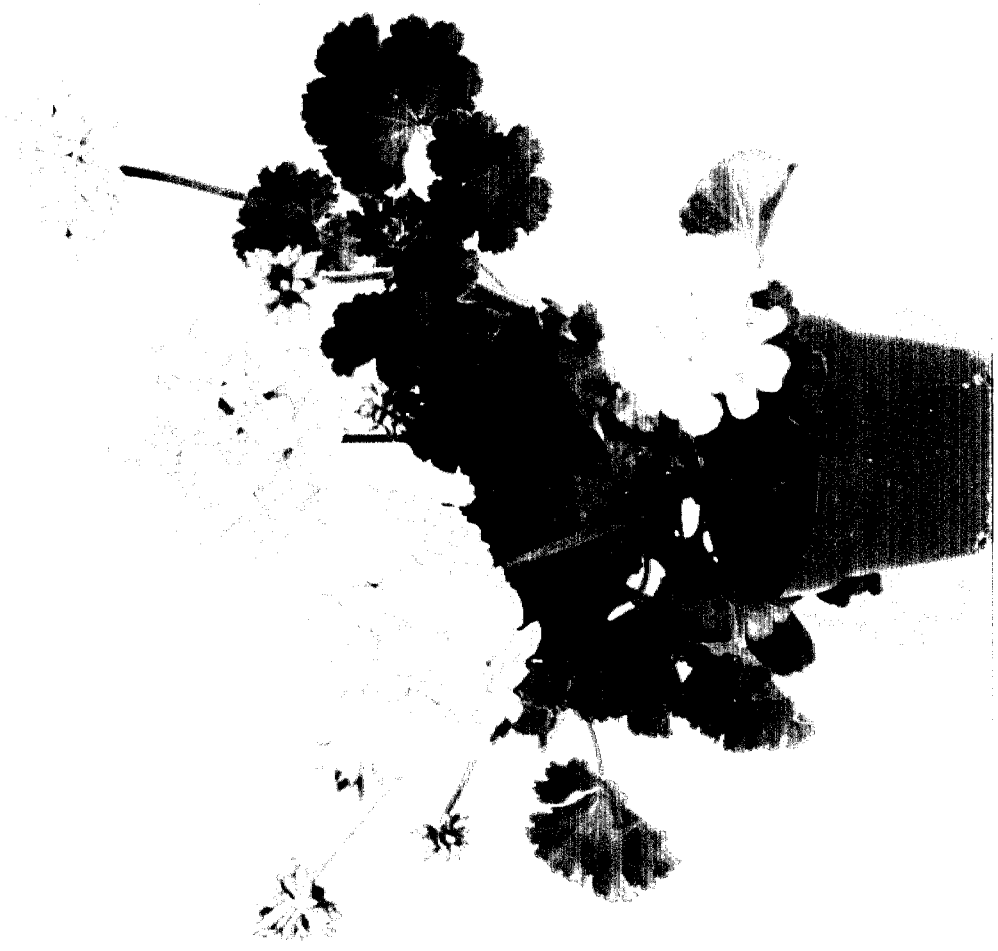

* * * * *